(12) United States Patent
Miller et al.

(10) Patent No.: US 8,465,466 B2
(45) Date of Patent: Jun. 18, 2013

(54) METHOD AND SYSTEM FOR NON-VASCULAR SENSOR IMPLANTATION

(75) Inventors: Michael E. Miller, Los Angeles, CA (US); Rajiv Shah, Rancho Palos Verdes, CA (US)

(73) Assignee: Medtronic MiniMed, Inc, Northridge, CA (US)

(*) Notice: Subject to any disclaimer, the term of this patent is extended or adjusted under 35 U.S.C. 154(b) by 2226 days.

(21) Appl. No.: 10/996,026

(22) Filed: Nov. 22, 2004

(65) Prior Publication Data

US 2005/0090866 A1 Apr. 28, 2005

Related U.S. Application Data

(62) Division of application No. 10/034,627, filed on Dec. 27, 2001, now Pat. No. 7,025,760.

(60) Provisional application No. 60/335,627, filed on Oct. 23, 2001.

(51) Int. Cl.
*A61M 31/00* (2006.01)
*A61K 9/22* (2006.01)

(52) U.S. Cl.
USPC ........................ 604/500; 604/891.1

(58) Field of Classification Search
USPC .............. 604/500, 27, 28, 503, 506, 890.1, 604/891.1, 892.1, 65–67
See application file for complete search history.

(56) References Cited

U.S. PATENT DOCUMENTS

| | | | |
|---|---|---|---|
| 3,731,681 A | 5/1973 | Blackshe et al. | |
| 3,923,060 A * | 12/1975 | Ellinwood, Jr. | ............ 604/891.1 |
| 4,003,379 A | 1/1977 | Ellinwood, Jr. | |
| 4,240,438 A | 12/1980 | Updike et al. | |
| 4,479,796 A | 10/1984 | Kallok | |

(Continued)

FOREIGN PATENT DOCUMENTS

| | | |
|---|---|---|
| JP | 02-071724 A | 3/1990 |
| JP | 05-504704 | 7/1993 |

(Continued)

OTHER PUBLICATIONS

Subminiature Implantable Potentiostat and Modified Commercial Telemetry Device for Remote Glucose Monitoring—IEEE Transactions on Instrumentation and Measurement, vol. 48. No. 6 Dec. 1999—Richard D. Beach Senior Member IEEE, Falko V. Kuster, and Francis Moussy, Member IEEE.

(Continued)

*Primary Examiner* — Manuel A Mendez
(74) *Attorney, Agent, or Firm* — Medtronic MiniMed, Inc.

(57) ABSTRACT

A method and system for non-vascular sensor implantation. An implant unit is implanted in an area of a body and a foreign body capsule is allowed to form around the area of the implant unit. The sensor may be directed into a body cavity such as, for example, the peritoneal space, subcutaneous tissues, the foreign body capsule, or other area of the body. A subcutaneous area of the body may be tunneled to place the sensor. The system may include an implant unit such as, for example, for delivering drug to a human body and a sensor for detecting a physiological parameter. The sensor may be separate from and connectable to the implant unit and may be placed in a non-vascular area of the human body.

20 Claims, 9 Drawing Sheets

U.S. PATENT DOCUMENTS

| | | | |
|---|---|---|---|
| 4,484,987 A | | 11/1984 | Gough |
| 4,568,335 A | | 2/1986 | Updike et al. |
| 4,596,575 A | | 6/1986 | Rosenberg et al. |
| 4,628,928 A | | 12/1986 | Lowell |
| 4,650,547 A | | 3/1987 | Gough |
| 4,703,756 A | | 11/1987 | Gough et al. |
| 4,721,677 A | | 1/1988 | Clark, Jr. |
| 4,734,184 A | | 3/1988 | Burleigh et al. |
| 4,757,022 A | | 7/1988 | Shults et al. |
| 4,771,772 A | | 9/1988 | DeWitt |
| 4,802,479 A | | 2/1989 | Haber et al. |
| 4,874,500 A | | 10/1989 | Madou et al. |
| 4,890,620 A | | 1/1990 | Gough |
| 4,911,168 A | | 3/1990 | Davis |
| 4,994,167 A | | 2/1991 | Shults et al. |
| 5,039,390 A | | 8/1991 | Hampp et al. |
| 5,094,951 A | | 3/1992 | Rosenberg |
| 5,139,485 A | | 8/1992 | Smith et al. |
| 5,266,688 A | | 11/1993 | Rosenberg |
| 5,300,106 A | | 4/1994 | Dahl et al. |
| 5,317,269 A | | 5/1994 | Mills et al. |
| 5,322,063 A | | 6/1994 | Allen et al. |
| 5,324,518 A | * | 6/1994 | Orth et al. ............ 424/423 |
| 5,328,460 A | | 7/1994 | Lord et al. |
| 5,357,969 A | | 10/1994 | Herleikson |
| 5,411,647 A | | 5/1995 | Johnson et al. |
| 5,497,772 A | | 3/1996 | Schulman et al. |
| 5,509,410 A | | 4/1996 | Hill et al. |
| 5,534,025 A | | 7/1996 | Moussy |
| 5,569,186 A | | 10/1996 | Lord et al. |
| 5,587,352 A | | 12/1996 | Tamura et al. |
| 5,593,852 A | | 1/1997 | Heller et al. |
| 5,660,163 A | | 8/1997 | Schulman et al. |
| 5,667,983 A | | 9/1997 | Abel et al. |
| 5,682,884 A | | 11/1997 | Hill et al. |
| 5,685,856 A | | 11/1997 | Lehrer |
| 5,691,932 A | | 11/1997 | Reiner et al. |
| 5,694,932 A | | 12/1997 | Michel |
| 5,696,314 A | | 12/1997 | McCaffrey et al. |
| 5,701,895 A | | 12/1997 | Prutchi et al. |
| 5,707,502 A | | 1/1998 | McCaffrey et al. |
| 5,711,868 A | | 1/1998 | Maley et al. |
| 5,728,281 A | | 3/1998 | Holmstrom et al. |
| 5,741,211 A | | 4/1998 | Renirie et al. |
| 5,741,319 A | | 4/1998 | Woloszko et al. |
| 5,770,028 A | | 6/1998 | Maley et al. |
| 5,773,270 A | | 6/1998 | D'Orazio et al. |
| 5,791,344 A | | 8/1998 | Schulman et al. |
| 5,804,048 A | | 9/1998 | Wong et al. |
| 5,919,216 A | | 7/1999 | Houben et al. |
| 5,932,175 A | | 8/1999 | Knute et al. |
| 5,941,906 A | | 8/1999 | Barreras, Sr. et al. |
| 5,965,380 A | | 10/1999 | Heller et al. |
| 5,985,129 A | | 11/1999 | Gough et al. |
| 5,987,352 A | | 11/1999 | Klein et al. |
| 5,992,211 A | | 11/1999 | Skrtic |
| 5,999,848 A | | 12/1999 | Gord et al. |
| 6,001,067 A | * | 12/1999 | Shults et al. ............ 600/584 |
| 6,002,954 A | | 12/1999 | Van Antwerp et al. |
| 6,027,479 A | | 2/2000 | Alei et al. |
| 6,049,727 A | | 4/2000 | Crothall |
| D424,696 S | | 5/2000 | Ray et al. |
| D426,638 S | | 6/2000 | Ray et al. |
| 6,075,610 A | | 6/2000 | Ueda et al. |
| 6,093,167 A | | 7/2000 | Houben et al. |
| 6,103,033 A | | 8/2000 | Say et al. |
| 6,120,676 A | | 9/2000 | Heller et al. |
| 6,122,536 A | | 9/2000 | Sun et al. |
| 6,125,290 A | | 9/2000 | Miesel |
| 6,125,291 A | | 9/2000 | Misel et al. |
| 6,134,459 A | | 10/2000 | Roberts et al. |
| 6,135,978 A | | 10/2000 | Houben et al. |
| 6,144,866 A | | 11/2000 | Miesel et al. |
| 6,159,240 A | | 12/2000 | Sparer et al. |
| 6,162,611 A | | 12/2000 | Heller et al. |
| 6,163,723 A | | 12/2000 | Roberts et al. |
| 6,175,752 B1 | | 1/2001 | Say et al. |
| 6,198,952 B1 | | 3/2001 | Miesel |
| 6,201,980 B1 | | 3/2001 | Darrow et al. |
| 6,206,871 B1 | | 3/2001 | Zanon et al. |
| 6,210,326 B1 | | 4/2001 | Ehwald |
| 6,233,471 B1 | | 5/2001 | Berner et al. |
| 6,248,080 B1 | | 6/2001 | Miesel et al. |
| 6,251,260 B1 | | 6/2001 | Heller et al. |
| 6,261,280 B1 | | 7/2001 | Houben et al. |
| 6,264,611 B1 | | 7/2001 | Ishikawa et al. |
| 6,268,161 B1 | | 7/2001 | Han et al. |
| 6,331,244 B1 | | 12/2001 | Lewis et al. |
| 6,402,689 B1 | * | 6/2002 | Scarantino et al. ........... 600/300 |
| 6,431,175 B1 | | 8/2002 | Penner et al. |
| 6,442,413 B1 | | 8/2002 | Silver |
| 6,558,321 B1 | | 5/2003 | Burd et al. |
| 6,692,520 B1 | | 2/2004 | Gambale et al. |
| 6,702,847 B2 | | 3/2004 | DiCarlo |
| 2001/0039374 A1 | | 11/2001 | Schulman |
| 2002/0055673 A1 | | 5/2002 | Van Antwerp et al. |
| 2002/0120186 A1 | | 8/2002 | Keimel |
| 2003/0050680 A1 | | 3/2003 | Gibson et al. |
| 2003/0078560 A1 | | 4/2003 | Miller et al. |
| 2003/0078650 A1 | | 4/2003 | Nunez et al. |

FOREIGN PATENT DOCUMENTS

| | | |
|---|---|---|
| JP | 5-238960 | 9/1993 |
| JP | 06-189915- | 7/1994 |
| JP | 6-189915 A | 7/1994 |
| JP | 6-277201 | 10/1994 |
| JP | 06-339532 | 12/1994 |
| JP | 8-154903 | 6/1996 |
| JP | 08-233774 | 9/1996 |
| JP | 09-512200 | 12/1997 |
| JP | 10-026585 A | 1/1998 |
| JP | 11-004895 A | 1/1999 |
| JP | 11-501234 | 2/1999 |
| JP | 11-508792 | 8/1999 |
| JP | 2000-515778 | 11/2000 |
| JP | 2001-510382 A | 7/2001 |
| JP | 2001-516980 | 10/2001 |
| JP | 2002-513602 A | 5/2002 |
| JP | 2002-525153 T | 8/2002 |
| WO | WO 92/07525 * | 5/1992 |
| WO | WO-92/07525 | 5/1992 |
| WO | WO-92/10141 A1 | 6/1992 |
| WO | WO-96/25089 A1 | 8/1996 |
| WO | WO 97/01986 | 1/1997 |
| WO | WO 98/01071 | 1/1998 |
| WO | WO 98/28605 | 7/1998 |
| WO | WO-99/13574 | 3/1999 |
| WO | WO 99/48419 | 9/1999 |
| WO | WO 99/56613 | 11/1999 |
| WO | WO-00/18294 A1 | 4/2000 |
| WO | WO 00/33065 | 6/2000 |
| WO | WO 01/01851 A * | 1/2001 |
| WO | WO-01/74251 A2 | 10/2001 |
| WO | WO 01/01851 A1 | 11/2001 |
| WO | WO-01/91846- | 12/2001 |
| WO | WO-02/50534 A1 | 6/2002 |

OTHER PUBLICATIONS

Supplemental European Search Report dated Dec. 17, 2008 for related European Patent Application No. 02780519.1-1265/1438029.

Decision of Rejection dated Dec. 9, 2008 for related Japanese patent application No. 2003-537480.

Office Action dated Jun. 23, 2009 from related patent application No. 10/334,686.

Office Action issued from related Japanese patent application No. 2003-537480.

International Search Report dated Mar. 14, 2005 for PCT Application No. PCT/US2003/029328.

International Search Report dated May 8, 2003 for PCT Application No. PCT/US2002/033923.

Notice of Allowance dated Aug. 31, 2005 from related U.S. Appl. No. 10/034,627.

Notice of Allowance dated Jan. 11, 2010 from related U.S. Appl. No. 11/286,471.

Office Action dated Jul. 21, 2009 from related JP patent application No. 2003-537480.

Office Action dated Aug. 22, 2006 for EP Application No. 03754703.1.

Office Action dated Aug. 5, 2009 from related U.S. Appl. No. 11/286,471.

Office Action dated Dec. 22, 2008 for JP Application No. 2003-537480.

Office Action dated Dec. 5, 2008 from related U.S. Appl. No. 10/334,686.

Office Action dated Dec. 8, 2009 for EP Application No. 03754703.1.

Office Action dated Jun. 23, 2006 from related U.S. Appl. No. 10/334,686.

Office Action dated Jun. 6, 2008 from related U.S. Appl. No. 10/334,686.

Office Action dated Mar. 14, 2005 from related U.S. Appl. No. 10/034,627.

Office Action dated Mar. 2, 2004 from related U.S. Appl. No. 10/034,627.

Office Action dated Mar. 24, 2009 for EP Application No. 02780519.1.

Office Action dated Mar. 8, 2007 from related U.S. Appl. No. 10/334,686.

Office Action dated Sep. 2, 2008 for JP application No. 2003-537480.

Office Action dated Sep. 6, 2007 from related U.S. Appl. No. 10/334,686.

The Office Action dated Feb. 19, 2008 for EP Application No. 03754703.1.

European Search Report dated Apr. 27, 2006 for EP Application No. 03754703.1.

Notice of Allowance dated Apr. 28, 2010 from related patent U.S. Appl. No. 10/334,686.

Office Action dated Nov. 9, 2010 from related European patent application No. 02 780 519.1.

Office Action dated Oct. 26, 2010 from related Japanese application No. 2003-537480.

Office Action dated Aug. 31, 2010 from related Japanese application No. 2004-540104.

Office Action dated Aug. 4, 2009 from related Japanese Application 2004-540104.

English description of relevance for Office Action dated Aug. 4, 2009 for related Japanese patent application 2004-540104.

* cited by examiner

METHOD AND SYSTEM FOR NON-VASCULAR SENSOR IMPLANTATION

CROSS-REFERENCE TO RELATED APPLICATIONS

This application is a divisional of application Ser. No. 10/034,627 filed Dec. 27, 2001, (now U.S. Pat. No. 7,025,760), which is in turn claims the benefit of prior filed U.S. Provisional Application Ser. No. 60/335,627 filed Oct. 23, 2001. The entirety of each which are incorporated herein by reference.

BACKGROUND

1. Field of the Invention

The present invention relates to the field of in vivo sensors and, in particular, to in vivo sensors that are implanted in non-vascular areas of the body.

2. Description of Related Art

Traditional methods of physiological parameter sensing typically rely on vascular placement of a physiological parameter sensor. Such placement permits a sensing element such as, for example, a biomolecule, to make direct contact with the blood, providing sensing capabilities of blood components. Such sensing capabilities have greatly facilitated analysis, diagnosis and treatment of many debilitating diseases and medical conditions.

However, vascular placement of a physiological parameter sensor may suffer from several disadvantages. A physiological parameter sensor is not inserted into a vein without great difficulty and painstaking effort by an attending physician. Moreover, a physiological parameter sensor is not adjusted within or extracted from a vein without similar difficulty and effort.

Furthermore, vascular placement of a physiological parameter sensor subjects the sensor to a constant fluid environment. Such an environment may have several detrimental effects on the sensor. Due to constant fluidic contact, the sensor may suffer from decreased sensitivity, stability and effective life. Should a characteristic of the sensor be diminished to an extent rendering the sensor ineffective, the sensor must be removed and replaced, introducing the difficulties for both patient and physician associated with such removal and replacement. To complicate matters, every time a physiological parameter sensor is removed and replaced, it must be disconnected and reconnected to an implant unit utilizing the sensor output.

In an effort to assuage some of the disadvantages associated with vascular implantation of physiological parameter sensors, integrated sensor/implant unit systems have been developed. Such systems may be placed in or near a body cavity and may provide non-vascular sensing of physiological parameters. However, the incision required for such sensor/implant unit systems is relatively large and the trauma in the area of implantation can be significant. Such trauma generally prevents sensing of physiological parameters. Because such trauma may not subside for several weeks or a month or even longer, pre-implantation analysis methods used by the patient must continue. Without continuation of preimplantation analysis methods, a patient may go undiagnosed and untreated for many weeks, possibly even a month or longer. Such delay in treatment and diagnosis could be harmful or even fatal for patients who need daily diagnosis and treatment.

SUMMARY OF THE DISCLOSURE

Embodiments of the present invention relate to systems and methods for non-vascular sensor implantation.

A method for non-vascular implant of a sensor may include implanting an implant unit in an area of a body; allowing a foreign body capsule to form around the area of the implant unit; and directing the sensor into the foreign body capsule.

Implanting an implant unit may include incising an area of the body large enough for the implant unit. Allowing a foreign body capsule to form may comprise inserting materials around the implant unit to promote growth characteristics. A material may be placed around the implant unit for promoting growth characteristics. The implant unit may include electronics and/or a pump. The electronics may be sensor electronic or other electronics. The electronics may be integrated with the pump or may be mutually exclusive from the pump.

The sensor may be attached to the implant unit. The sensor may be attached to the implant unit prior to formation of the foreign body capsule or may be attached to the implant unit subsequent to formation of the foreign body capsule.

The method may further include incising an area of the body large enough for the sensor. The incised area of the body large enough for the sensor is smaller than an incised area of the body large enough for the implant unit.

A method for non-vascular implant of a sensor may also include incising an area of a body large enough for inserting an implant unit; incising an area remote from a sensor location for inserting a sensor; directing the sensor into a body cavity; connecting the sensor to the implant unit; and inserting the implant unit into the body. The method may further include fixing the sensor in place using suture. The implant unit may be inserted into a pocket formed when incising an area of the body large enough for inserting the implant unit.

Systems for non-vascular implant may include an implant unit for delivering drug to a human body and a sensor for detecting a physiological parameter. The sensor may be separate from and connectable to the implant unit and the sensor is placed in a non-vascular area of the human body.

The implant unit may include a pump and/or electronics. The drug delivered by the implant unit may be insulin. The sensor may include a biomolecule, a lead and a sensing element. The sensing element may be a biomolecule and the biomolecule may be a glucose oxidase enzyme. The physiological parameter sensed may be oxygen or glucose. The non-vascular area of the human body where the sensor is placed may be the peritoneum or subcutaneous tissue.

Embodiments of the present invention may also include a method for non-vascular implant of a sensor including incising an area of a body large enough for inserting an implant unit; creating a tunnel in subcutaneous tissue; directing the sensor through the tunnel; connecting the sensor to the implant unit; and inserting the implant unit into the body. The tunnel may be created using a blunt instrument such as, for example, a trocar, or other blunt instrument which does not cause trauma to the subcutaneous tissue.

These and other objects, features, and advantages of embodiments of the invention will be apparent to those skilled in the art from the following detailed description of embodiments of the invention when read with the drawings and appended claims.

DETAILED DESCRIPTION

In the following description of preferred embodiments, reference is made to the accompanying drawings which form a part hereof, and in which are shown by way of illustration specific embodiments in which the invention may be practiced. It is to be understood that other embodiments may be utilized and structural changes may be made without departing from the scope of the preferred embodiments of the present invention.

Figure 1:
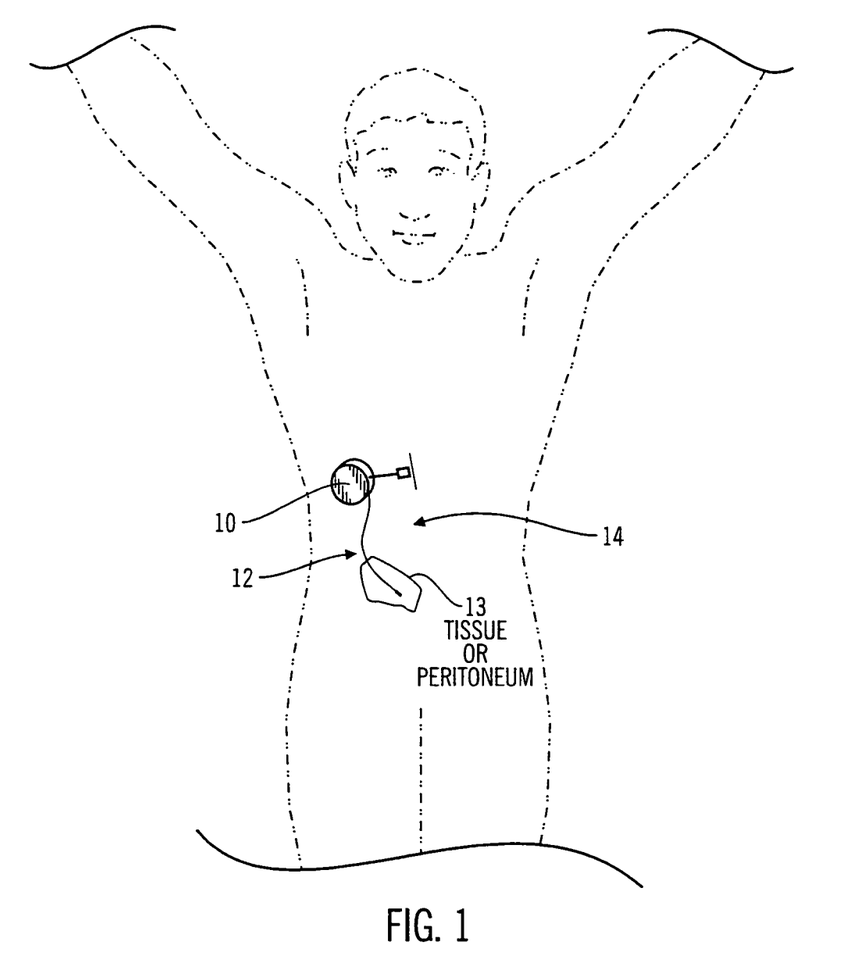
FIG. 1 shows a general position of an implant unit and a sensor in the human body according to an embodiment of the present invention.

FIG. 1 shows a general placement of an implant unit 10 and a sensor 12 in the human body according to an embodiment of the present invention. The implant unit 10 may be placed into a human body in a variety of locations such as, for example, adjacent to the abdominal cavity 14, or in other locations such as, for example, the spinal cavity or chest cavity. A sensor 12 connecting to the implant unit 10 may be located in the peritoneum 13, the membrane lining the abdominal cavity and connecting and supporting internal organs; in subcutaneous tissue 13, i.e., tissue beneath the skin; in a foreign body capsule; or in another area of the body. For example, the sensor 12 may be implanted into the shoulder area.

The implant unit 10 may contain electronics for data acquisition, data storage, data processing or other functions as may be required for physiological parameter sensing. In addition, the implant unit 10 may also contain, for example, a drug delivery system including a drug reservoir and a pumping mechanism to move a drug from the reservoir to a patient through, for example, a delivery catheter. The sensor 12 may sense a variety of physiological parameters. For example, the sensor 12 may sense glucose and oxygen and may be used in connection with the implant unit 10 to pump insulin for diabetics.

Figure 2:
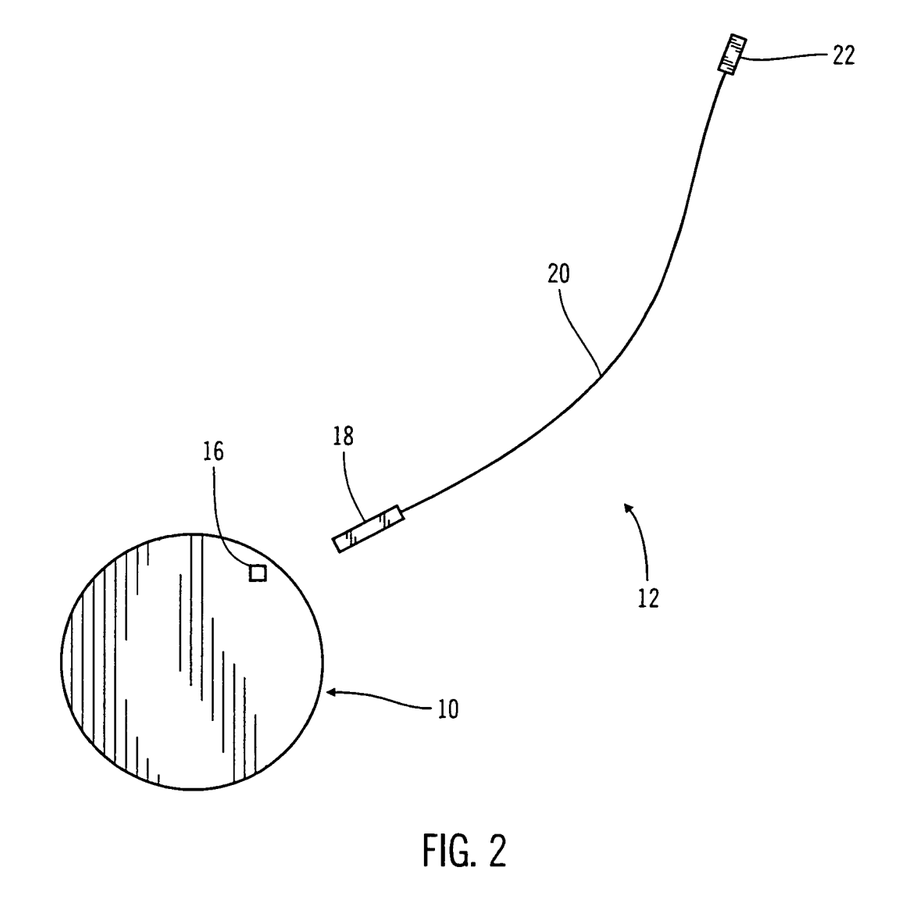
FIG. 2 shows a generalized implant unit and a sensor according to an embodiment of the present invention.

FIG. 2 shows a generalized implant unit 10 and a sensor 12 according to an embodiment of the present invention. The implant unit 10 and the sensor 12 are not integrated. They are discreet devices and may or may not be used independently of one another. The implant unit 10 and the sensor 12 may be used in conjunction with one another and may be inserted into a patient at separate times. The ability to insert the implant unit 10 and the sensor 12 into a patient at different times gives physicians and patients enhanced flexibility when implanting the devices.

As can be seen in FIG. 2, the sensor 12, according to an embodiment of the present invention, includes a connector 18, a sensor lead 20 connected to the connector at one end, and a sensing element 22 connected to the sensor lead 20 at another end. Thus, the sensing element 22 of the sensor 12 may be located away from the implant unit 10 which, as will be seen shortly, offers enhanced functionality in sensing physiological parameters.

As shown in FIG. 2, according to an embodiment of the present invention the implant unit 10 may include a receptacle 16 for accepting the connector 18 portion of the sensor 12. Also, the sensor lead 20 is not limited to any particular length. For example, the sensor lead 20 may be approximately nine inches long, permitting the sensing element 22 to be approximately nine inches from the implant unit 10. However, the sensor lead 20 may be longer or shorter than nine inches depending on the application and the particular placement of the sensing element 22 desired.

Also, the implant unit 10 may include its own lead that connects to the sensor lead 20. Thus, rather than connecting the sensor lead 20 to the receptacle 16, the sensor lead 20 may connect to an implant unit lead.

Figure 3A:
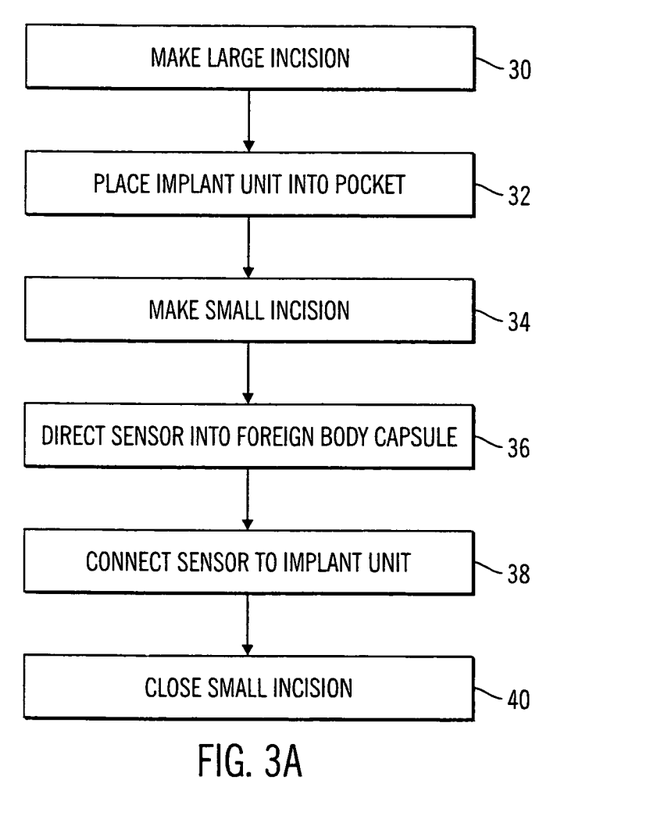
FIG. 3A shows a process for making a non-vascular placement of a sensor into a foreign body capsule according to an embodiment of the present invention

FIG. 3A shows a process for making a non-vascular placement of the sensor 12 into a foreign body capsule according to an embodiment of the present invention. At step 30, a large incision may be made in the body at a desired or convenient location for the implant unit 10. While making the incision of step 30, a pocket may be made in the subcutaneous tissue that is large enough to support the implant unit 10. At step 32, the implant unit 10 may be inserted into the subcutaneous tissue pocket. The pocket may then be closed.

Once the implant unit 10 has been inserted into the subcutaneous tissue pocket and the pocket has been closed, the implant unit 10 may be left in the body for a period of time long enough that a foreign body capsule forms around the implant unit 10. The implant unit 10 may need to be left undisturbed in its position in the body for up to several weeks, a month, or longer in order to allow the foreign body capsule to form. The foreign body capsule is made up of scar tissue, primarily collagen and fibrin.

During the period when the foreign body capsule is forming, a sensor 12 may or may not be attached to the implant unit 10. If a sensor 12 is not attached to the implant unit 10, it may still be possible to use the implant unit 10 in an open-loop configuration. For example, if the implant unit 10 contains telemetry circuitry, it may be possible to communicate with the implant unit 10 form a remote location. For example, if the implant unit 10 is an insulin pump, and no sensor 12 is attached to the implant unit 10 during the period in which the foreign body capsule is forming around the implant unit 10, the patient may still analyze his or her insulin levels by traditional methods, such as, for example, using a home analysis system to take a blood sample and analyze the levels of insulin in the blood. If it is determined that the patient needs a dosage of insulin, and if the insulin pump which has been placed into the patient's body is equipped with telemetry electronics, the patient may communicate with the insulin pump telemetrically using a portable transmitting unit and command the pump to deliver a dosage of insulin. Thus, the patient may begin to immediately use the insulin pump, without having a sensor 12 attached to the pump, in an open-loop configuration. Thus, using embodiments of the present invention, there is no need to wait for the foreign body capsule to form around the implant unit 10 before making use of the implant unit 10.

An oxygen sensor may be used in the vicinity of the foreign body capsule to determine if the foreign body capsule has formed and the area has healed. Generally, no oxygen will be detected during formation of the foreign body capsule.

Once the foreign body capsule has formed around the implant unit 10, at step 34 a small incision may be made in the vicinity of the implant unit 10 pocket allowing access to the receptacle 16 of the implant unit 10. If a sensor has been previously connected to the implant unit 10, it may be disconnected at this time. After the small incision has been made and any previously connected sensors have been disconnected from the implant unit, at step 36 the sensor 12 may be directed into the foreign body capsule. The sensing element 22 may be introduced into the foreign body capsule surrounding the implant unit through the small incision made at step 34. The sensing element 22 may be placed within the foreign body capsule. The connector 18 may reside in the subcutaneous pocket created for the implant unit 10 by the body.

In addition, a silicone plug may be used to plug the receptacle so that it remains open during the period of time the foreign body capsule is forming around the implant unit. If a silicone plug has been inserted into the receptacle 16, it may also be removed at this time.

At step 38, the sensor 12 may be connected to the implant unit 10 at the receptacle 16 on the implant unit 10 designed for connecting to the sensor 12 by connecting the connector 18 to the receptacle 16. Once the sensor 12 has been connected to the implant unit 10, the small incision may be closed at step 40. At this point, the implant unit 10 and the sensor 12 may be used in a closed-loop configuration. For example, if the implant unit 10 is an insulin pump and the sensing element 22 of the sensor 12 contains a glucose oxidase enzyme for sensing glucose and oxygen in order to determine insulin levels in the patient, the glucose and oxygen levels and, consequently, the insulin levels in the patient may be determined by the sensing element 22 in the foreign body capsule. Vascular placement of the sensor 12 is not required.

Figure 3B:
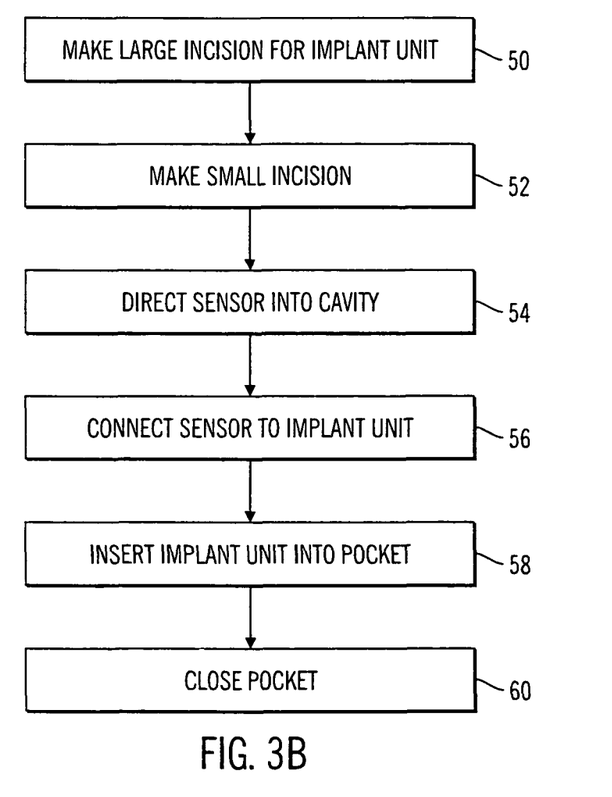
FIG. 3B shows a process for making a non-vascular placement of a sensor into a body cavity such as, for example, the peritoneal space, according to an embodiment of the present invention.

FIG. 3B shows a process for making a non-vascular placement of the sensor 12 into a body cavity such as, for example, the peritoneal space, according to an embodiment of the present invention. At step 50, a large incision may be made in the body at a desired or convenient location for the implant unit 10. While making the incision of step 50, a pocket may be made in the subcutaneous tissue above the cavity to be used that is large enough to support the implant unit 10.

After the large incision has been made for the implant unit 10 at step 50, at step 52 a small incision may be made in a muscle wall of the cavity such as, for example, the peritoneal space, for allowing implantation of the sensor 12. The small incision may be far or remote from final placement of the sensor 12. After the small incision has been made, at step 54 the sensor 12 may be directed into the cavity. The sensing element 22 may be introduced into the cavity through the small incision made at step 52. The connector 18 may reside in the subcutaneous pocket created for the implant unit 10 by the body.

At step 56, the sensor 12 may be connected to the implant unit 10 at the receptacle 16 on the implant unit 10 designed for connecting to the sensor 12 by connecting the connector 18 to the receptacle 16. Once the sensor 12 has been connected to the implant unit 10, at step 58 the implant unit 10 may be inserted into the subcutaneous tissue pocket created at step 50. After the implant unit 10 has been inserted into the subcutaneous tissue pocket, the pocket may be closed at step 60. As before, at this point the implant unit 10 and the sensor 12 may be used in a closed-loop configuration.

Figure 3C:
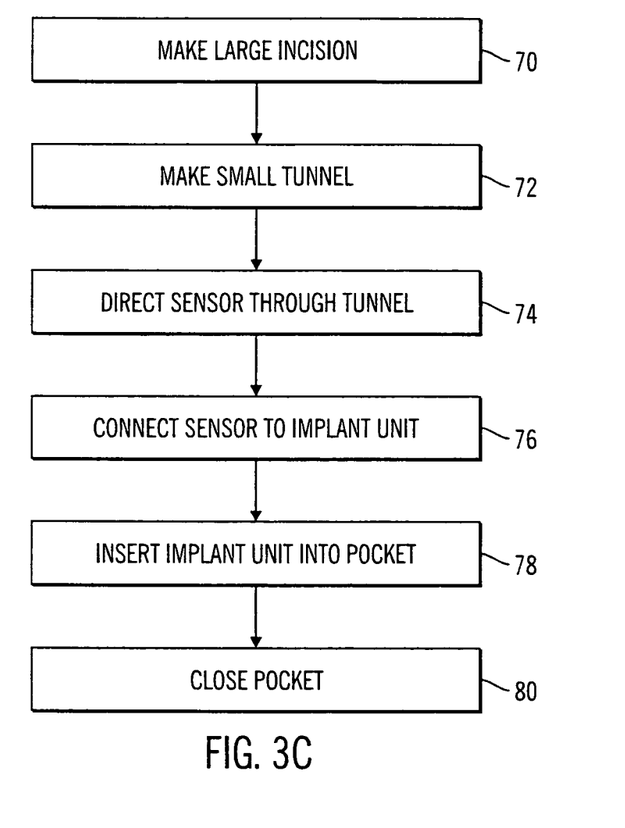
FIG. 3C shows a process for making a non-vascular placement of a sensor into subcutaneous tissue according to an embodiment of the present invention.

FIG. 3C shows a process for making a non-vascular placement of the sensor 12 into subcutaneous tissue according to an embodiment of the present invention. At step 70, a large incision may be made in the body at a desired or convenient location for the implant unit 10. While making the incision of step 70, a pocket may be made in the subcutaneous tissue above the cavity to be used that is large enough to support the implant unit 10.

After the large incision has been made for the implant unit 10 at step 70, at step 72 a small tunnel may be made for the sensor at the edge of pocket created for the implant unit 10. An incision for the tunnel may be made far or remote from final placement of the sensor 12. The tunnel may be made using a blunt, minimally traumatic tissue implant. The sensor 12 may be tunneled through the subcutaneous tissue by starting at an edge of the implant unit 10 pocket and tunneling into the subcutaneous tissue parallel to the skin. It may be desirable to stay within the subcutaneous tissue while tunneling. If the blunt, minimally traumatic tissue implant device used includes an introducer, the introducer may be left in the subcutaneous tissue while the remaining portion of the blunt, minimally traumatic tissue implant device may be removed.

After the tunnel has been made, at step 74 the sensing element 22 of sensor 12 may be directed into the introducer of the blunt, minimally traumatic tissue implant device. The connector 18 may reside in the subcutaneous pocket created for the implant unit 10 by the body. If it is desired that the sensor be fixed in its location, suture tabs such as, for example, those used on pacing leads or long term catheters may be used.

At step 76, the sensor 12 may be connected to the implant unit 10 at the receptacle 16 on the implant unit 10 designed for connecting to the sensor 12 by connecting the connector 18 to the receptacle 16. Once the sensor 12 has been connected to the implant unit 10, at step 78 the implant unit 10 may be inserted into the subcutaneous tissue pocket created at step 70. After the implant unit 10 has been inserted into the subcutaneous tissue pocket, the pocket may be closed at step 80. As before, at this point the implant unit 10 and the sensor 12 may be used in a closed-loop configuration.

Figure 4:
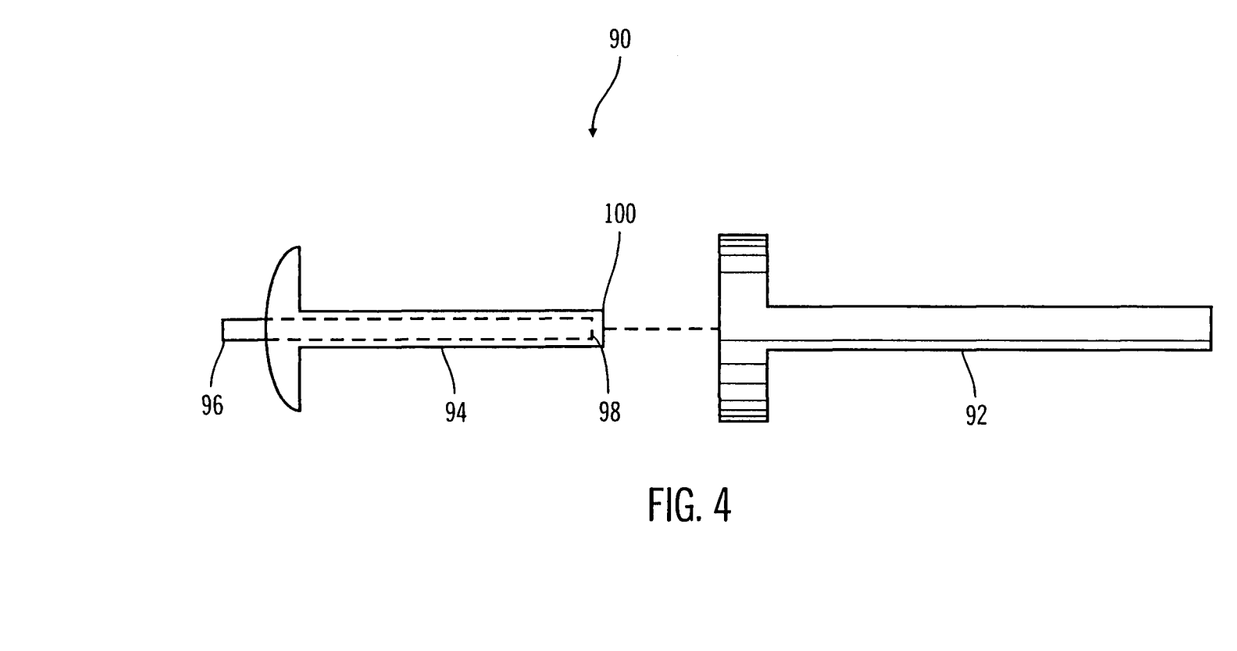
FIG. 4 shows a biopsy trocar used according to an embodiment of the present invention.

The blunt, minimally traumatic tissue implant device used to tunnel the sensor 12 into a subcutaneous region may be a biopsy trocar 90 shown generally in FIG. 4. As shown in FIG. 4, the biopsy trocar 90 includes an introducer 92 into which the main body 94 of the trocar 90, having a sharp end 100, and a secondary body 96 of the trocar 90, having a blunt end 98, may be inserted. The introducer 92 may be made of plastic while the main body 94 and the secondary body 96 may be made of metal. The secondary body 96 having the blunt end 98 may be inserted into the main body 94 having the sharp end 100, and both the secondary body 96 and the main body 94 may be inserted into the introducer 92. All three portions of the trocar 90 may then be tunneled into the subcutaneous tissue. The sharp end 100 of the main body 94 of the trocar 90 may make an initial incision, while the blunt end 98 of the secondary body 96 may tunnel through the subcutaneous tissue. By tunneling through the subcutaneous tissue with the blunt end 98 of the secondary body 96, less damage occurs to the subcutaneous tissue than would occur if the subcutaneous tissue were tunneled with the sharp end 100 of the main body 94, resulting in less bleeding and less trauma to the tissue and the patient. Once the end of the trocar 90 has reached the desired location for the sensing element 22 of the sensor 12, the main body 94 and the secondary body 96 are removed from the introducer 92. The sensor 12 is then guided through the introducer 92 so that the sensing element 22 eventually arrives at its desired location. The introducer 92 may then be removed from the body and the connector 18 may then be connected to the implant unit 10. Because the sensing element 22 of the sensor 12 is not located in the vicinity of the main incision that was made to insert the implant unit 10, the difficulties associated with obtaining a signal from the sensing element 22 due to the trauma of the area are avoided. Because the sensing element 22 is located away from the implant unit 10 incision, there is nothing to prevent obtaining a signal from the sensing element 22 in a very short period of time. For example, after the sensor 12 has been tunneled into the subcutaneous tissue and connected to the implant unit 10, it may possible to obtain a signal from the sensing element 22 within 24 hours of sensor 12 placement. Thus, for example, if the implant unit 10 is an insulin pump and the sensing element 22 of the sensor 12 is a glucose oxidase enzyme for sensing insulin levels in diabetics, automated insulin analysis and insulin delivery in a diabetic patient may be feasible within 24 hours of in vivo implantation of the implant unit 10 and the sensor 12.

If so desired, a variety of materials may be placed around the implant unit 10 or sensor 12 to promote different characteristics of the foreign body capsule or sensor area. For example, if it is desired to grow more blood vessels in the area of the foreign body capsule or sensor 12, the implant unit 10 or sensor 12 may be covered with GORE-TEX or PTFE. Other materials may also be used to cover the implant unit 10 or sensor 12 depending on the nature of the characteristics of the foreign body capsule or area around the sensor 12 desired. In addition, various chemicals may be pumped into the area of the foreign body capsule in order to promote different characteristics of the foreign body capsule, such as, for example, blood vessel growth.

The sensor 12 may be inserted into the body by tunneling into a subcutaneous region using a biopsy trocar 60 shown generally in FIG. 5. As shown in FIG. 5, the biopsy trocar 60 includes an introducer 50 into which the main body 52 of the trocar 60, having a sharp end 58, and a secondary body 54 of the trocar 60, having a blunt end 56, may be inserted. The introducer 50 may be made of plastic while the main body 52 and the secondary body 54 may be made of metal. The secondary body 54 having the blunt end 56 may be inserted into the main body 52 having the sharp end 58, and both the secondary body 54 and the main body 52 may be inserted into the introducer 50. All three portions of the trocar 60 may then be tunneled into the subcutaneous tissue. The sharp end 58 of the main body 52 of the trocar 60 may make an initial incision, while the blunt end 56 of the secondary body 54 may tunnel through the subcutaneous tissue. By tunneling through the subcutaneous tissue with the blunt end 56 of the secondary body 54, or for that matter, any device which is used for minimally traumatic implantation, less damage occurs to the subcutaneous tissue than would occur if the subcutaneous tissue were tunneled with the sharp end 58 of the main body 52, resulting in less bleeding and less trauma to the tissue and the patient. Once the end of the trocar 60 has reached the desired location for the sensing element 22 of the sensor 12, the main body 52 and the secondary body 54 are removed from the introducer 50. The sensor 12 is then guided through the introducer 50 so that the sensing element 22 eventually arrives at its desired location. The introducer may then be removed from the body and the connector 18 may then be connected to the implant unit 10. Because the sensing element 22 of the sensor 12 is not located in the vicinity of the main incision that was made to insert the implant unit 10, the difficulties associated with obtaining a signal from the sensing element 22 due to the trauma of the area are avoided. Because the sensing element 22 is located away from the implant unit 10 incision, there is nothing to prevent obtaining a signal from the sensing element 22 in a very short period of time. For example, after the sensor 12 has been tunneled into the subcutaneous tissue and connected to the implant unit 10, it may possible to obtain a signal from the sensing element 22 within 24 hours of sensor 12 placement. Thus, for example, if the implant unit 10 is an insulin pump and the sensing element 22 of the sensor 12 is a glucose oxidase enzyme for sensing insulin levels in diabetics, automated insulin analysis and insulin delivery in a diabetic patient may be feasible within 24 hours of in vivo implantation of the implant unit 10 and the sensor 12.

The implant unit 10 and the sensor 12 are modular units and may connect to each other via a mechanical interface. Because of the modularity of the implant unit 10 and the sensor 12, the sensor 12 may be removed or replaced without removing the implant unit 10. Thus, due to the small size of the sensor 12, only a small incision is required and trauma to the patient is minimized. No large incision is necessary to remove the implant unit 10 unless the implant unit 10 itself needs to be removed or replaced.

Figure 5A:
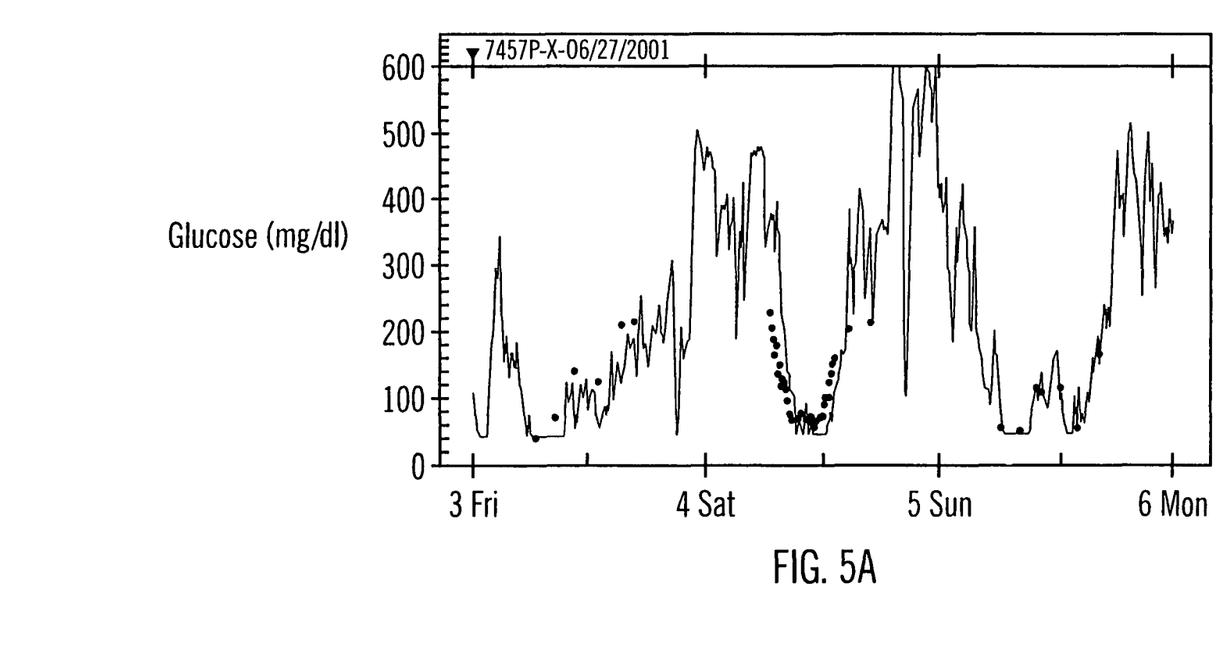
FIG. 5A shows glucose data over a period of several days for a sensor implanted into a foreign body capsule according to an embodiment of the present invention.
Figure 5B:
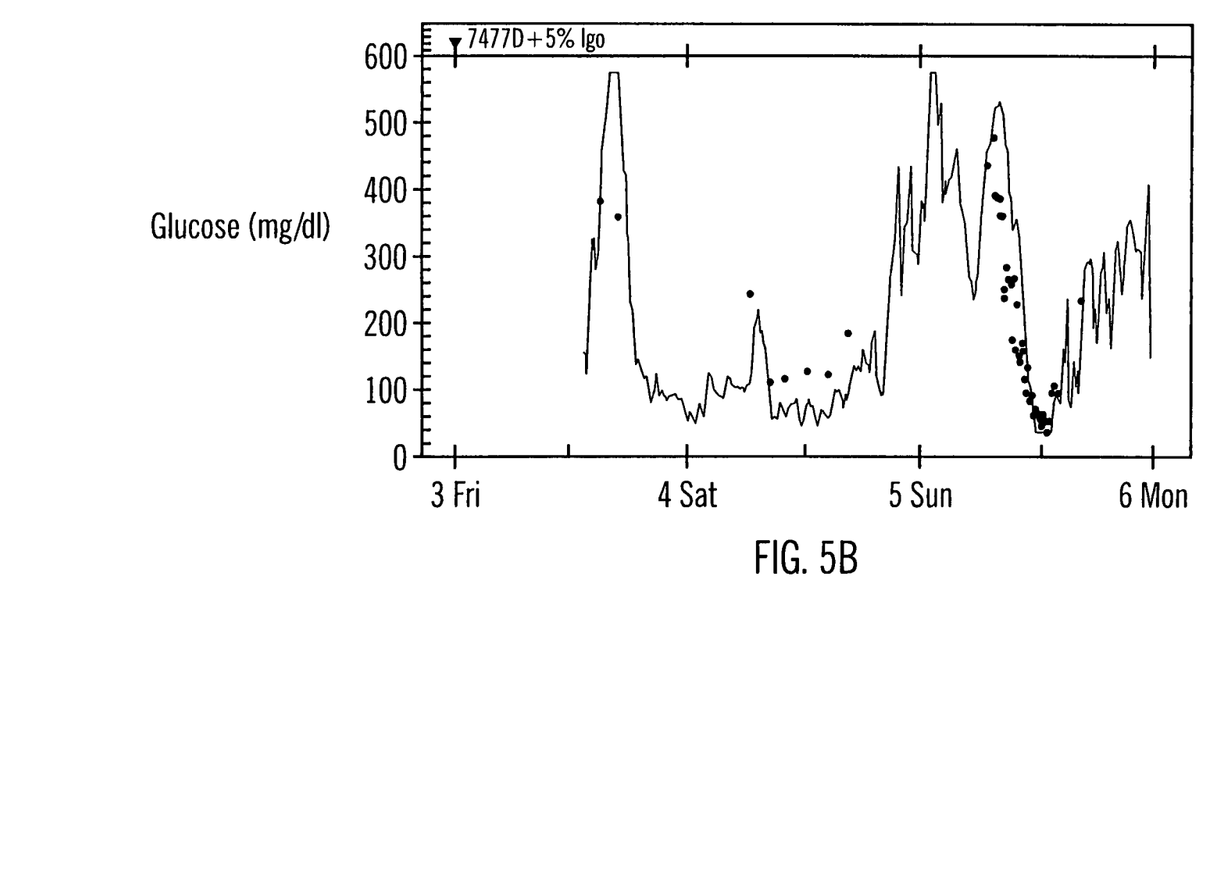
FIG. 5B shows glucose data over a period of several days for a sensor implanted into subcutaneous tissue according to an embodiment of the present invention.
Figure 5C:
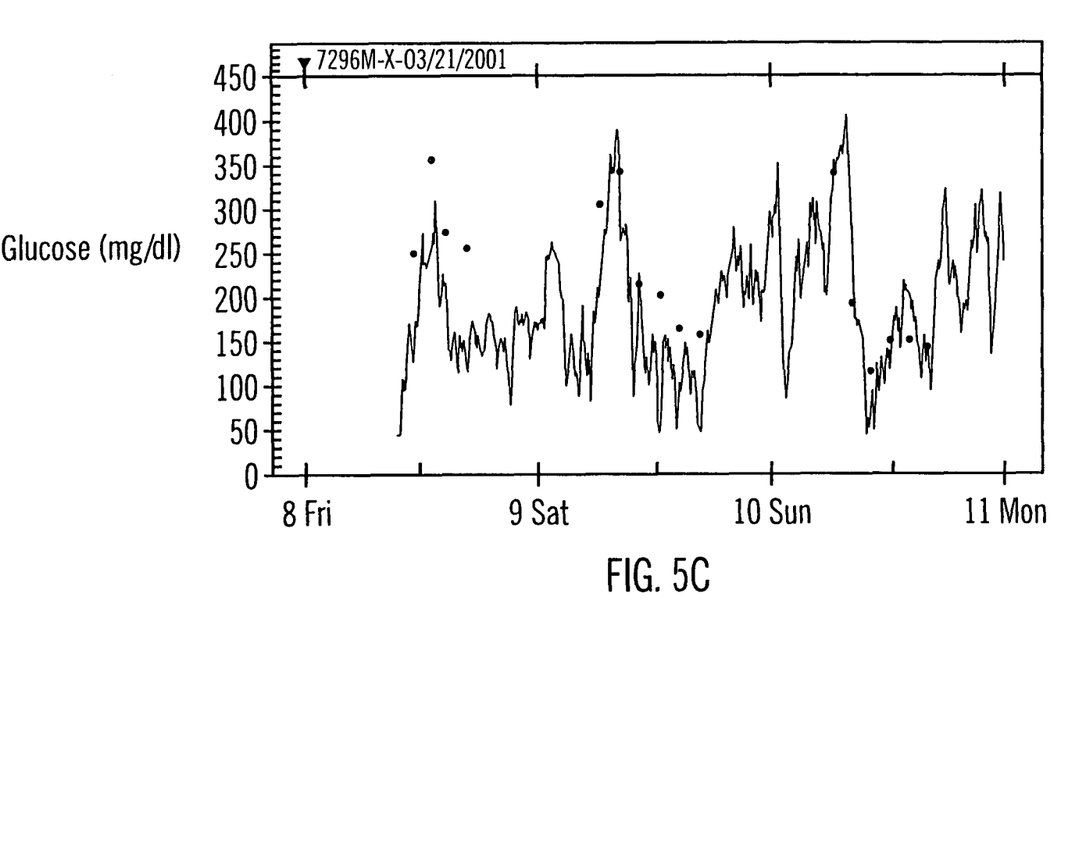
FIG. 5C shows glucose data over a period of several days for a sensor implanted into a body cavity such as a peritoneal space according to an embodiment of the present invention.

Data for sensors used in glucose sensing applications may be seen in FIGS. 5A, 5B and 5C. In FIG. 5A, glucose data over a period of several days for a sensor implanted into a foreign body capsule may be seen. In FIG. 5B, glucose data over a period of several days for a sensor implanted into subcutaneous tissue may be seen. In FIG. 5C, glucose data over a period of several days for a sensor implanted into a body cavity such as a peritoneal space may be seen.

While particular embodiments of the present invention have been shown and described, it will be obvious to those skilled in the art that the invention is not limited to the particular embodiments shown and described and that changes and modifications may be made without departing from the spirit and scope of the appended claims.

What is claimed is:

1. A method for non-vascular implant of a sensor comprising:
   implanting an implant unit in an area of a body capable of forming a foreign body capsule without passing the implant unit through a vascular system;
   allowing a foreign body capsule to form around the area of the implant unit;
   directing a sensor into the foreign body capsule; and
   connecting the sensor to the implant unit subsequent to formation of the foreign body capsule.

2. The method of claim 1, wherein implanting an implant unit comprises incising an area of the body large enough for the implant unit.

3. The method of claim 1, further comprising placing a material around the implant unit for promoting growth characteristics.

4. The method of claim 1, wherein the implant unit comprises electronics.

5. The method of claim 1, wherein the implant unit comprises a pump.

6. The method of claim 1, wherein allowing a foreign body capsule to form comprises inserting materials around the implant unit to promote growth characteristics.

7. The method of claim 1, further comprising attaching the sensor to the implant unit.

8. The method of claim 7, wherein the sensor is attached to the implant unit prior to formation of the foreign body capsule.

9. The method of claim 7, wherein the sensor is attached to the implant unit subsequent to formation of the foreign body capsule.

10. The method of claim 1, further comprising incising an area of the body large enough for the sensor.

11. The method of claim 10, wherein the incised area of the body large enough for the sensor is smaller than an incised area of the body large enough for the implant unit.

12. The method of claim 1, wherein implanting the implant unit includes inserting the implanting unit into an incision and closing the incision.

13. The method of claim 1, wherein the sensor is located away from the location of the implant unit area.

14. The method of claim 1, wherein the area of the body capable of forming a foreign body capsule includes abdominal, spinal or chest cavities.

15. The method of claim 1, wherein directing the sensor into the foreign body capsule is performed after the formation of the foreign body capsule.

16. The method of claim 1, wherein directing the sensor into the foreign body capsule comprises making a small incision in the foreign body capsule to allow access to the implant unit.

17. The method of claim 1, wherein allowing a foreign body capsule to form includes waiting a sufficient time after implanting the implant unit for the formation of the foreign body capsule.

18. A method for non-vascular implant of a sensor comprising:

implanting an implant unit in a body cavity capable of forming a foreign body capsule;

allowing a foreign body capsule to form around the implant unit;

directing a sensor into the foreign body capsule; and connecting the sensor to the implant unit subsequent to formation of the foreign body capsule.

19. The method of claim 18, wherein implanting the implant unit includes, inserting the implanting unit into an incision and closing the incision.

20. The method of claim 18, wherein the body cavity capable of forming a foreign body capsule includes abdominal cavity, spinal cavity or chest cavity.

\* \* \* \* \*